United States Patent [19]

Wunderling et al.

[11] Patent Number: 5,251,633
[45] Date of Patent: Oct. 12, 1993

[54] OPTICAL PROBE

[75] Inventors: Martin Wunderling, Boeblingen; Lothar Rupp, Kirchstrasse; Martin Guenther, Wildberg, all of Fed. Rep. of Germany

[73] Assignee: Hewlett-Packard Company, Palo Alto, Calif.

[21] Appl. No.: 742,596

[22] Filed: Aug. 8, 1991

[30] Foreign Application Priority Data

Aug. 13, 1990 [EP] European Pat. Off. ........ 90115496.3

[51] Int. Cl.$^5$ ............................................. A61B 5/00
[52] U.S. Cl. ...................... 128/634; 128/635; 128/637
[58] Field of Search .................. 128/634, 637, 635; 356/39–41

[56] References Cited

U.S. PATENT DOCUMENTS

| 5,020,537 | 6/1991 | Günther | 128/634 |
| 5,047,208 | 9/1991 | Schweitzer et al. | 128/634 |
| 5,047,627 | 9/1991 | Yim et al. | 128/634 |
| 5,054,882 | 10/1991 | Riccitelli et al. | 128/634 |
| 5,056,520 | 10/1991 | Tomisaka et al. | 128/634 |
| 5,098,659 | 3/1992 | Yim et al. | 128/634 |
| 5,143,066 | 9/1992 | Komives et al. | 128/634 |

FOREIGN PATENT DOCUMENTS

| 0279004 | 8/1988 | European Pat. Off. | 128/634 |
| 0336984 | 10/1989 | European Pat. Off. | |
| 0336985 | 10/1989 | European Pat. Off. | 128/634 |
| 8605589 | 9/1986 | World Int. Prop. O. | 128/634 |

OTHER PUBLICATIONS

S. R. Goldstein et al., "A Miniature Fiber Optic pH Sensor for Physiological Use", *Journal of Biomechanical Engineering*, May 1980, vol. 102, pp. 141–146.

J. L. Gehrich et al., "Optical Fluorescence and Its Application to an Intravascular Blood Gas Monitoring System", *IEEE Transactions on Biomedical Engineering*, Feb. 1986, No. 2, pp. 117–132.

Primary Examiner—Randall L. Green
Assistant Examiner—Gina M. Gualtieri
Attorney, Agent, or Firm—Woodcock Washburn Kurtz Mackiewicz & Norris

[57] ABSTRACT

An improved optical probe for the invasive measurement of partial carbon dioxide pressures is disclosed that minimizes $pCO_2$ reading drift. An optical probe for the invasive measurement of the partial carbon dioxide pressure comprises an optical fiber and a $pCO_2$ sensor. The $pCO_2$ sensor comprises a diffusion zone with a dye-containing gel that is optically sensitive to $H^+$ ions and a semi-permeable membrane that is permeable to $CO_2$ molecules, but is substantially nonpermeable to hydrogen ions Components of the $pCO_2$ sensor, such as the part of the optical fiber extending into the sensor or a reflector, are covered with a substance—preferably with a coating—that is substantially nonpermeable to hydrogen ions. This prevents the hydrogen ions from diffusing into the sensor components, which otherwise would cause an imbalance of hydrogen ions and, therefore, a drift in the $pCO_2$ reading.

15 Claims, 2 Drawing Sheets

OPTICAL PROBE

BACKGROUND OF THE INVENTION

The present invention relates to an optical probe for the invasive measurement of at least the partial carbon dioxide pressure (pCO$_2$) of a biologic circulatory system.

Probes for the invasive measurement of blood parameters usually consist of at least one sensor that is connected with an associated monitor via an optical fiber. Typically, such probes comprise between 1 and 3 sensors, e.g., intended for the measurement of blood gases such as partial oxygen pressure (pO$_2$) or partial carbon dioxide pressure (pCO$_2$), or for the measurement of the pH value of the blood. All these sensors have a similar mechanical construction. The optical fiber in each sensor ends with a gel containing a dye. The optical density or another optical parameter of the dye varies with the blood parameter to be measured. Light emitted by the associated monitor and transmitted via the optical fiber is fed into the gel and passes through it. The light is then fed back via the same or another optical fiber to the monitor, which contains a detector to measure light attenuation or changes in other optical parameters caused by the dye. This attenuation or change is a function of the blood parameter to be measured, and the relationship between attenuation, absorbance, or the change of another optical parameter and the blood parameter is well-known.

Usually, a reflector is positioned adjacent to the dye-containing gel, opposite to the optical fiber. In such a sensor, light transmitted through the optical fiber passes the gel, is reflected at the reflector, passes the gel again and is then transmitted back. In this environment, only one optical fiber is required for each sensor. Further, as the light passes the dye-containing gel twice, it is easier to detect any change in the optical characteristics of that dye. However, there are also other alternatives such as directing the light to a second optical fiber (when it has passed the gel) and feeding the second optical fiber back to the monitor. The key point in all of these cases is that the light has to pass the gel zone where its optical characteristics are altered.

The end of the fiber, the gel, and the reflector are surrounded by a semi-permeable or selective membrane (for example, a hydrogen ion permeable envelope in the case of a pH sensor). This membrane permits, on the one hand, only selected ions or molecules to reach the dye-containing gel; on the other hand, it has a mechanical function, namely to keep the gel in place.

In this description, and as it is usual in the art, the region of the dye-containing gel, together with the part of the membrane in this region, is called the "diffusion zone."

Optical probes as described herein usually comprise three or more sensors in order to measure various blood parameters with one probe. In these cases, the single optical fibers associated with the respective sensors are combined in a single cable for connection with the associated monitor. However, it is also possible to build an optical probe with one or two sensors only. Optical probes can be introduced into a patient's artery to measure—depending on the dye—various blood parameters such as pH, pO$_2$ or pCO$_2$, as described above. It is also possible to integrate further components such as a strain-relieving wire, an arterial pressure sensor or the like into the probe.

There have been attempts to use plastic fibers in pH sensors in the early days of the development of intravascular blood sensors. See "A Miniature Fiber Optic pH Sensor for Physiological Use," Journal of Biomedical Engineering, May 1980, pages 141 et seq. Nobody proposed to use them, however, in pO$_2$ or pCO$_2$ sensors. Subsequently, plastic fibers were generally not used due to their transmission characteristics. Instead, glass fibers were used (see "Optical Fluorescence and its Application to an Intravascular Blood Gas Monitoring System," IEEE Transactions on Biomedical Engineering, Vol. BME-33, No. 2, February 1986, pages 117, 119).

For a more detailed description of invasive fiber optic blood parameter measurement, reference is made to "Optical Fluorescence and its Application to an Intravascular Blood Gas Monitoring System," IEEE Transactions on Biomedical Engineering, Vol. BME-33, No. 2, February 1986, pages 117 et seq., and "A Miniature Fiber Optic pH Sensor for Physiological Use," Journal of Biomedical Engineering, May 1980, pages 141 et seq. Examples of the construction of an optical probe incorporating multiple sensors are described in European patent applications 2 79 004, 3 36 984, and 3 36 985.

The field of the present invention deals with pCO$_2$ sensor probes. PCO$_2$ sensors use the same dye and the same gel as pH sensors, namely a dye that is sensitive to H$^+$ ions. The major difference between a pH sensor and a pCO$_2$ sensor is that, in the case of a pH sensor, the selective membrane surrounding the sensor is permeable to H$^+$ ions, whereas, in the case of a pCO$_2$ sensor, the membrane is permeable to CO$_2$ molecules (and not to H$^+$ ions). According to the following, simplified equation:

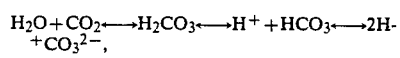

$$H_2O + CO_2 \leftrightarrow H_2CO_3 \leftrightarrow H^+ + HCO_3^- \leftrightarrow 2H^+ + CO_3^{2-},$$

CO$_2$ molecules penetrating into the dye-containing gel increase the number of available H$^+$ ions, which, in turn, changes the optical characteristics of the dye. Therefore, the pCO$_2$ sensor in essence measures a pH change that is caused by a change in the pCO$_2$.

Extensive series of tests have shown that the known pCO$_2$ sensors show a time-dependent drift even when the external CO$_2$ pressure applied to the sensor is held constant. More specifically, if the external CO$_2$ pressure is increased by a certain amount (e.g., by means of a step function), the pCO$_2$ reading based on the pCO$_2$ sensor is initially correct but then shows a deviation over time leading to inaccurate measurement results.

Turning now in detail to the drawings of the prior art, FIG. 1 depicts a typical system of the prior art for the invasive measurement of blood parameters, for example of the partial carbon dioxide pressure (pCO$_2$). The light of an optical transmitter 1 is directed into an optical fiber 2 (see arrow 2a), here a glass fiber. Usually a train of light pulses is used, but this is not a strict requirement. The light passes an optical coupler 3 and reaches tip 4 of the sensor, the tip being intended for introduction into the artery of a patient. Tip 4 of the sensor contains a gel into which a dye such as phenolred is immobilized. The dye modifies at least one optical parameter, preferably the intensity, of the light in an amount dependant on the pCO$_2$ (or, in other cases, the pO$_2$ or the pH) value of the blood. The modified light is reflected into the same fiber and, after passing through optical coupler 3, reaches an optical receiver 5 (see arrow 5a). It is understood that optical transmitter 1 and optical receiver 5 are incorporated into a monitor or other measuring instrument 8. Dashed line 6 indicates a releasable connection between the probe 7 and the monitor 8. Thus, the optical probe 5 consists of an optical fiber as well 30 as at least a $pCO_2$ sensor. As will be shown in more detail below, the optical probe comprises usually a multiplicity of sensors and optical fibers.

FIG. 2 depicts a longitudinal section of the probe tip 9 of an optical probe comprising three sensors. A sheath 10 is closed at its outer end (proximal end) with a metal cap 11 and connected, as shown by 12, with a tubing element 13. The connection between sheath 10 and tubing element 13 is secured by adhesive means Tubing element 13 ends at a connector for connection to an appropriate monitor (not shown).

Sheath 12 contains three sensors, two of which are shown in FIG. 2, namely a pH sensor 14 and a $pCO_2$ sensor 15. A third sensor, namely a $pO_2$ sensor, is not shown in FIG. 2 as it is hidden behind $pCO_2$ sensor 15.

Each of the sensors is connected with the associated monitor via an optical fiber, as shown by optical fiber 16 (which is surrounded by an appropriate envelope 17) for the case of pH sensor 14 and optical fiber 18 for the $pCO_2$ sensor 15 (surrounded by envelope 19). The various sensors are fastened within sheath 10 by means of a silicone glue or adhesive 20.

Sheath 10 further comprises three openings, the first of which is labeled as 21 in FIG. 2, whereas the second opening 22 is hidden behind the $pCO_2$ sensor 15. The third opening is not shown in FIG. 2; it is contained in the broken-away part. These openings ensure that, when the probe tip is introduced into a patient's artery, the sensors are in contact with the blood, thus allowing gas molecules and hydrogen ions to reach the sensors.

$PCO_2$ sensor 15 further comprises a dye-containing gel 23 and an optical reflector 24. The region where dye-containing gel 23 is located is also called the "diffusion zone." Sensor 15 is, insofar as contained in sheath 10, surrounded by a semi-permeable membrane 25 that is fixed on optical fiber 18 and reflector 24 by means of a further glue or adhesive, as will be explained later.

In similar manner, pH sensor 14 comprises a dye-containing gel 26, a reflector 27, and a semi-permeable membrane 28.

It is understood that the probe of FIG. 2 is only one example of an invasive optical blood parameter probe. In other embodiments, the probe can comprise only one or two sensors, or even more elements, such as a strain relieving wire.

The operation of the sensors will now be explained by means of FIG. 3, which shows a longitudinal section through a $pCO_2$ sensor 15. The mechanical construction of $pCO_2$ sensor 15 is typical for sensors of this type; the $pO_2$ and the pH sensor have a similar construction.

$PCO_2$ sensor 15 comprises a glass fiber 18 and an optical reflector 24. Optical reflector 24 is made of stainless steel, and its surface 29 is polished. Between the optical fiber and the reflector, a gel 23 is located. This gel is used to immobilize a dye such as phenolred, the optical characteristics of which varies with the blood parameter—in this case, $CO_2$—to be measured. The sensor 15 is surrounded by a semi-permeable or selective membrane 25 that is fastened onto the sensor 15 by means of a glue 30. This selective membrane 25 is permeable to the ions or gas molecules to be measured.

In the case of a $pCO_2$ sensor 15, the selective membrane 25 is permeable to $CO_2$ molecules.

In operation, light guided in optical fiber 18 reaches dye-containing gel 23, the absorption spectrum of the dye (for example, phenolred) being dependent on the pH value. In accordance with the equation

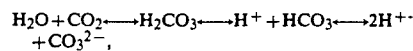

a change in the concentration of $CO_2$ molecules causes a change in the concentration of $H^+$ ions, which in turn alters the optical characteristics of the dye.

The light is then reflected at the polished surface 29 of optical reflector 24. It passes the dye-containing gel 23 again in reverse direction and is then fed back into optical fiber 18. The associated monitor measures the intensity of the reflected light to determine the pH change and thus the $pCO_2$ change. The preferred material for selective membrane 30 is—in case of a $pCO_2$ sensor—polypropylene comprising a silicone coating.

FIG. 4 is a graph illustrating a typical drift effect of a $pCO_2$ sensor. This diagram has been recorded in a test environment, i.e., the $pCO_2$ sensor has been exposed to an artificial $CO_2$ environment. Dashed line 31 indicates the partial carbon dioxide pressure of the artificial environment, whereas continuous line 32 depicts the sensor response, i.e., the $pCO_2$ reading of a sensor. The abscissa shows the time scaled in hours, whereas the ordinate shows the partial carbon dioxide pressure (scaled in kPa as well as in Torr).

The graph shows that the $pCO_2$ sensor reacts accurately when the external $pCO_2$ value is suddenly increased at t=10 hours, i.e., the $pCO_2$ reading is 13.33 kpa, as is the external carbon dioxide pressure (reference number 33). However, although the external $CO_2$ pressure is held constant over the next four hours, the $pCO_2$ reading of the sensor shows a significant drift or deviation over this time period. That is, the indicated $pCO_2$ value deviates more and more from the externally applied value.

A similar effect can be observed when the external $CO_2$ pressure is reduced to 2.67 kPa at t=14 hours. The $pCO_2$ reading of the sensor depicts a significant undershoot at this point in time (reference number 34); during the next four hours, the reading returns again to the external value.

Accordingly, there exists a need for an improved $pCO_2$ sensor that will provide an accurate $pCO_2$ reading irrespective of time.

SUMMARY OF THE INVENTION

It is, therefore, an objective of the present invention to provide an optical probe with a $pCO_2$ sensor that gives an accurate reading irrespective of time and, in particular, shows little or no drift.

In accordance with this invention, the problem of $pCO_2$ reading drift is solved in an optical probe of the kind described above in that at least a part of the sensor that is in H communication with the dye-containing gel comprises, in addition to the semi-permeable membrane that is permeable to $CO_2$ and substantially impermeable to $H^+$ ions, a substance that is substantially impermeable to $H^+$ ions. Such a substance prevents $H^+$ ions from diffusing into components of the $pCO_2$ sensor protected by such coating or mixing so that the amount of available $H^+$ ions in the diffusion zone of the $pCO_2$ sensor remains constant. Consequently, the sensor will show significantly reduced drift. This increases the accuracy and reliability of the sensor and the probe.

Any substance suited to preventing H+ ions from diffusing into the components of the sensor can be used, either by coating these components or by using an appropriate mixture. Alternatively, the components themselves can be made of materials that do not allow significant H+ diffusion.

Other objects, aspects, and advantages of the invention will be apparent to those skilled in the art upon the reading of the specification and the appended claims.

DETAILED DESCRIPTION OF PREFERRED EMBODIMENTS

Figure 1:
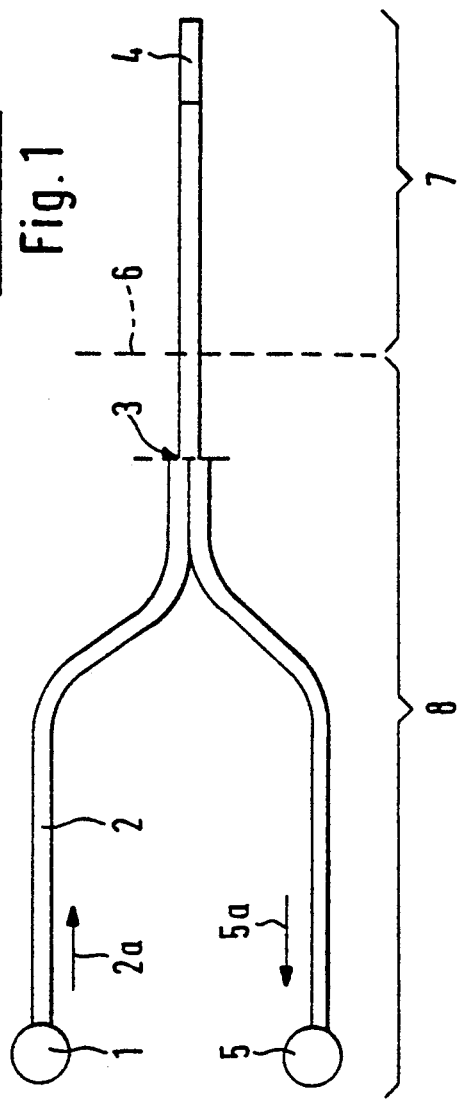
FIG. 1 depicts the basic operating principle of a prior art optical system for the invasive measurement of blood parameters.
Figure 2:
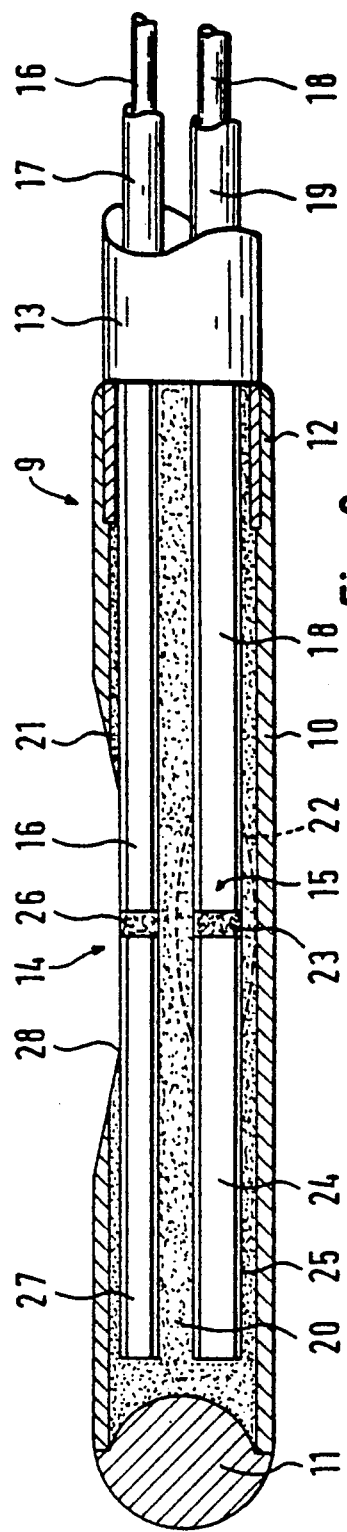
FIG. 2 is a longitudinal section of a prior art optical probe comprising a multiplicity of blood parameter sensors.

It has now been recognized that, in a $pCO_2$ sensor of the type described above, H+ ions may diffuse in various mechanical components and parts of the $pCO_2$ sensor, particularly in components consisting of glass. The result of such diffusion is a reduction of H+ ions in the diffusion zone, which causes an increase of the pH value and, therefore, a decrease of the measured $pCO_2$ value. Consequently, although an increase of the externally applied $CO_2$ pressure causes a corresponding increase of the measured $pCO_2$ value, the measured $pCO_2$ value then shows a drift over time to lower $pCO_2$ values.

This effect is only present in the $pCO_2$ sensor, not in the pH sensor. The reason is that the $pCO_2$ sensor constitutes, with regard to the H+ ions, a closed system, i.e. diffusion of H+ ions into various sensor components leads to a decrease of the number of available H+ ions. Such a decrease is not compensated. On the contrary, the pH sensor is covered with a membrane permeable to H+ ions, so that a decrease in H+ ions in the diffusion zone leads to an increase in H+ ion transport from the environment through the membrane to the dye-containing gel. In other words, the pH sensor is—in contrast to the $pCO_2$ sensor—an "open system" with respect to the H+ ions.

According to the present invention, the problem of $pCO_2$ reading drift is solved in an optical probe of the kind described above in that at least a part of the sensor that is in contact with the dye-containing gel is covered by, or mixed with, a substance that is basically impermeable to H+ ions. Such coating or mixing ("mixing" in this sense means a physical mixture as well as a chemical compound) prevents H+ ions from diffusing into components of the $pCO_2$ sensor protected by such coating or mixing. Therefore, the amount of available H+ ions in the diffusion zone of the $pCO_2$ sensor remains constant so that the sensor shows negligible drift. This increases the accuracy and reliability of the sensor and the probe.

The inventive effect may be obtained by any substance suited to preventing H+ ions from diffusing into the components of the sensor, either by coating these components or by using an appropriate mixture. It is also possible to coat only those parts or components of the sensor that show a considerable tendency to attract H+ ions, or simply to coat all components of the sensor.

Extensive tests have shown that glass is the most crucial material when considering unwanted H+ diffusion. In all known $pCO_2$ sensors, glass fibers have been used for the optical transmission between the monitor and the probe. The glass fiber extends into the sensor and is in contact with the dye-containing gel.

The tests revealed that the most significant effects, in terms of reduction of the drift, can be obtained if the part of the glass fiber extending into the sensor is coated with a material that is basically impermeable to H+ ions. The appropriate coating of a glass fiber is therefore a major aspect of the present invention.

Nevertheless, there are further components of the sensor that influence the $CO_2$ drift. An important component in this respect is the optical reflector contained in most $pCO_2$ sensors. This reflector is preferably made of metal, e.g., platinum or stainless steel. It is typically arranged opposite to the fiber with respect to the dye-containing gel. The surface facing the gel is usually polished. However, there are alternative embodiments, like using a glass reflector with an evaporated reflective film or the like. In an advantageous embodiment of the present invention, such reflector is also covered with a coating that is basically impermeable to H+ ions, thus reducing the $CO_2$ drift.

Surprisingly, it has further been found that the drift can also be reduced if the optical fibers are made of plastic, i.e., by using a plastic fiber. The present invention makes use of plastic fibers, despite possible disadvantages due to their transmission characteristics, in a $pCO_2$ sensor, as the advantage obtained in avoiding the $CO_2$ drift exceeds any possible transmission loss.

It is understood that, even if plastic fibers are used, a coating covering the proximal portion of the fiber may further reduce the drift.

Another part of the $pCO_2$ sensor influencing the drift characteristics is the glue usually used to fasten the semi-permeable membrane onto the sensor. Mixing this glue (physically or chemically) with a substance that prevents diffusion of H+ ions, or composing the glue of such a substance, further reduces drift of measured $CO_2$ values.

A coating used to make the components of the $pCO_2$ sensor resistant against hydrogen ion diffusion can be obtained in different ways. For example, tests have shown that a reduction of the drift may be obtained by the use of hexamethyldisilazane (HMDS) on the surface of a glass fiber. This leads to a chemical bonding of functional groups to the glass surface that makes it hydrophobic. Other silylating agents can be used as well.

An even larger improvement can be obtained by using a silicone or a copolymer of silicone and polycarbonate for coating the glass fiber. Tests have shown that such coating reduces the measurable drift by a factor of four to five.

While examples have been given, it should be emphasized that the present invention is not limited to a certain kind of coating or mixing. The present invention relates to any material suited to preventing hydrogen ions from diffusing into the components of the $pCO_2$ sensor.

The present invention also relates to a method for manufacturing an optical probe, wherein at least the proximal portion of the optical fiber and/or the optical reflector are covered with a coating that is basically impermeable to H+ ions before the pCO2 sensor and the optical probe are assembled.

Figure 4:
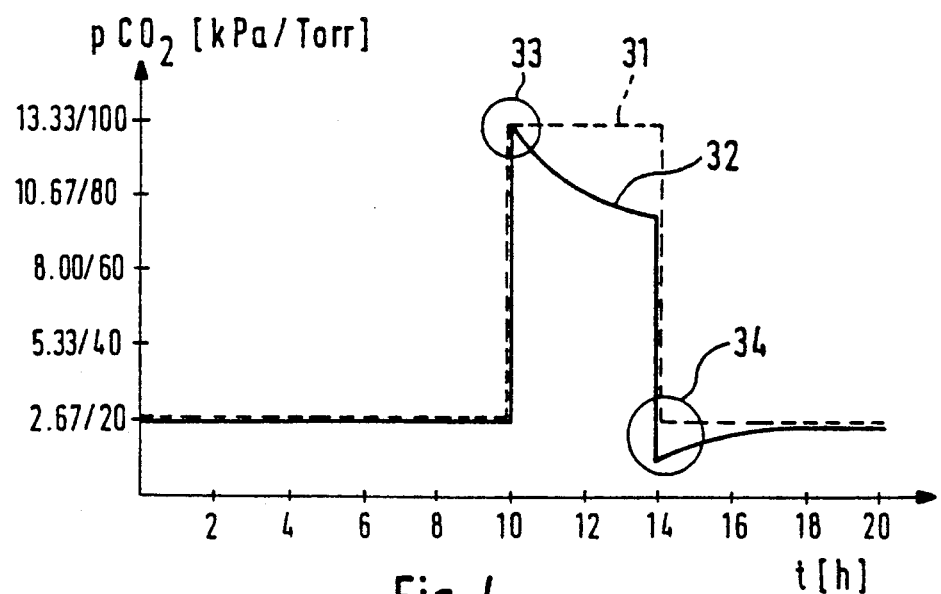
FIG. 4 is a graph depicting the effect of $CO_2$ drift in a prior art $pCO_2$ sensor.

It is an important finding of the present invention that the drift effects as shown in FIG. 4 are caused by the diffusion of H+ ions into certain components of the sensor, particularly the glass fiber, but also the reflector. As the pCO2 sensor is a closed system with respect to H+ ions—i.e. the imbalance caused by diffusion of H+ ions is not compensated by further supply of H+ ions from the environment (this is the case because only CO2 molecules, and no H+ ions, pass the semi-permeable membrane)—the diffusion of H+ ions leads to a reduction of H+ ions available in the diffusion zone and, therefore, to an increase of the pH value, which is equivalent to a decrease in the indicated pCO2 pressure.

The present invention overcomes this problem by coating the optical fiber and/or the reflector with a coating that is substantially impermeable to H+ ions. A sensor manufactured in this way is shown in longitudinal section in FIG. 5.

Figure 3:
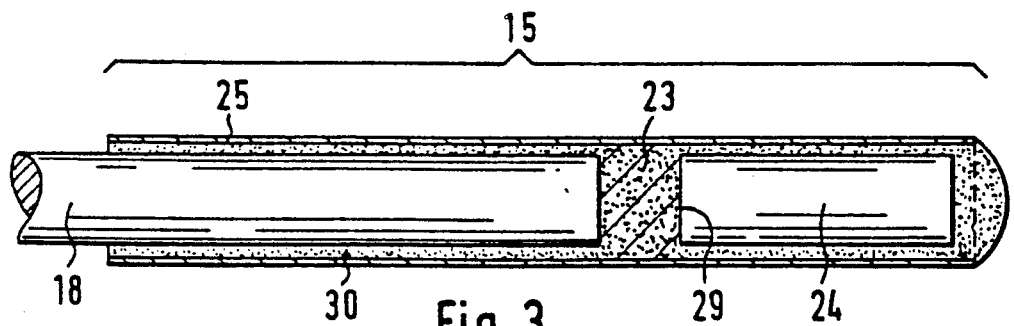
FIG. 3 is a longitudinal section of a prior art $pCO_2$ sensor comprised in the probe of FIG. 2.
Figure 5:
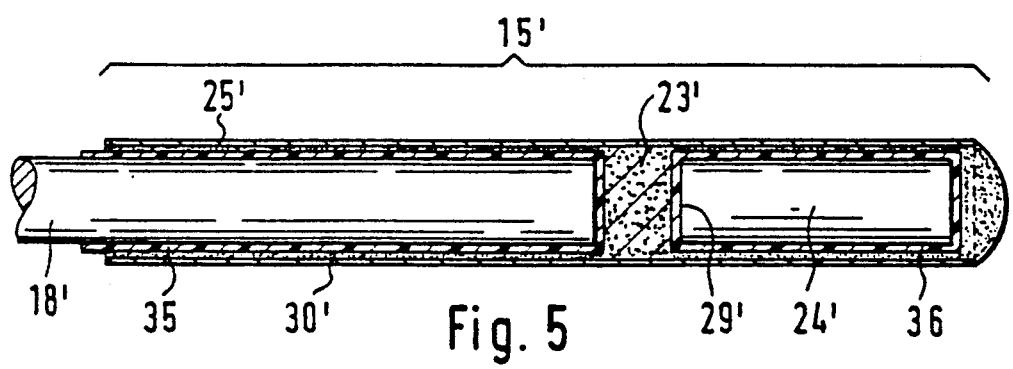
FIG. 5 depicts a $pCO_2$ sensor for use in a probe according to the present invention.

The reference numbers in FIG. 5 are the same as in FIG. 3 with the exception of an additional apostrophe, in order to indicate that the components of the two depicted sensors are basically the same. The major difference is that, in the environment of FIG. 5, the part of optical fiber 18' extending into the sensor is covered by a coating 35. Likewise, the reflector 24' is covered by a coating 36.

The major property of coatings 35 and 36 is that they are substantially impermeable to H+ ions. Thus, hydrogen ions can be prevented from diffusing into the components surrounded by such coatings. This stabilizes the pCO2 sensor and avoids the drift effect shown in FIG. 4.

Preferred materials for coatings 35 and 36 are PS099, a copolymer consisting of silicone and polycarbonate, as well as PS254, a similar copolymer. A reduction of the CO2 drift can also be obtained by the use of hexamethyldisilazane, which modifies the glass surface by the bonding of functional groups such that it becomes hydrophobic. The term "coating" as used in this specification includes such modification of a surface.

The effect of such coating has been verified in a standardized test. In this test, the externally applied CO2 was increased from 3% to 15%, and then the average drift of the pCO2 sensor reading over the first 12 hours was determined. The test revealed the following average drift values:

| Material | Average drift |
| --- | --- |
| Glass fiber without coating | 3.87 kPa/12h = 29 Torr/12h |
| Glass fiber with nonhygroscopic surface (Hexamethyldisilazane) | 2.8 kPa/12h = 21 Torr/12h |
| Glass fiber with PS099 coating | 1.07 kPa/12h = 8 Torr/12h |
| Glass fiber with PS254 coating | 0.8 kPa/12h = 6 Torr/12h |

The present invention is not limited to the use of the substances mentioned above. Other coatings can be used so long as the substance chosen is suited to preventing hydrogen ions from diffusing into the sensor components. Further, it is not mandatory to coat all of the sensor components in order to reduce the drift drastically.

As an alternative embodiment, H+ ions may also be prevented from diffusing into sensor components by using an appropriate physical or chemical mixture for the sensor components or glue 25'. Still further, the optical fiber may also be a plastic fiber, either coated or uncoated (FIGS. 3 or 5). In the case of an uncoated plastic fiber, the above-mentioned standardized test revealed the following results:

| Material | Average drift |
| --- | --- |
| Plastic fiber without coating | 1.2 kPa/12h = 9 Torr/12h |

Thus, an improved optical probe for the invasive measurement of partial carbon dioxide pressures is disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. An optical probe for the invasive measurement of at least the pCO2 of a biologic circulatory system comprising:
   a pCO2 sensor including
   (a) a sensing diffusion zone comprising a gel containing a dye that is optically sensitive to H+ ions; and
   (b) components coupled to said gel including an optical element having an end portion in optical communication with the gel; and
   a semi-permeable membrane at least partially enclosing said pCO2 sensor and said gel and components and comprising a material permeable to CO2 molecules but substantially impermeable to H+ ions;
   wherein at least one of said components is covered by a coating comprising a substance that is substantially impermeable to H+ ions.

2. The optical probe of claim 1 wherein said coating covers said end portion of said optical element.

3. The optical probe of claim 1 further comprising an optical reflector optically coupled to said optical element and a coating covering said optical reflector that is substantially impermeable to H+ ions.

4. The optical probe of claim 3 wherein said optical reflector comprises a metal.

5. The optical probe of claim 1, wherein said coating comprising a substance that is substantially impermeable to H+ ions is an adhesive for fastening said semi-permeable membrane to said gel and components.

6. The optical probe of claim 1 wherein said substance that is substantially impermeable to H+ ions is silicone or a copolymer of silicone and polycarbonate.

7. The optical probe of claim 1 wherein the substance that is substantially impermeable to H+ ions is hexamethyldisilazane or other silylating agent.

8. The optical probe of claim 1 wherein said adhesive is the coating that covers said at least one of said components.

9. An optical probe for the invasive measurement of at least the pCO2 of a biologic circulatory system comprising:
   a pCO2 sensor, said sensor having a diffusion zone with a dye-containing gel that is optically sensitive to H+ *ions*;
   a semi-permeable membrane that is permeable to CO2 molecules but substantially impermeable to H+ ions at least partially enclosing said diffusion zone;

an optical fiber comprising a plastic material extending into the pCO$_2$ sensor and through said semi-permeable membrane including an end portion of said plastic optical fiber juxtaposed with said dye-containing gel; and a coating covering at least said end portion of the plastic optical fiber extending into the pCO$_2$ sensor that comprises a substance that is substantially impermeable to H+ ions.

10. The optical probe of claim 9 further comprising an adhesive for fastening the semi-permeable membrane to said sensor, said adhesive comprising a substance that is substantially impermeable to H+ ions.

11. The optical probe of claim 9 wherein the substance that is substantially impermeable to H+ ions is silicone or a copolymer of silicone and polycarbonate.

12. The optical probe of claim 9 wherein the substance that is substantially impermeable to H+ ions is hexamethyldisilazane or other silylating agent.

13. A method for manufacturing an optical probe for the invasive measurement of at least the pCO$_2$ of a biologic circulatory system including an optical component and a diffusion zone with dye-containing gel that is optically sensitive to H+ ions enclosed within a semi-permeable membrane that is permeable to CO$_2$ molecules but substantially impermeable to H+ ions, said method comprising the steps of:

coating said optical component with a substance substantially impermeable to H+ ions before the optical probe is assembled; and assembling the optical component such that the optical component is in juxtaposition to the gel within said semi-permeable membrane.

14. The method of claim 13 wherein said probe includes a semi-permeable membrane that is permeable to CO$_2$ molecules and substantially impermeable to H+ ions, said method further comprising the step of adhesively fastening said membrane to said optical components and diffusion zone using a substance substantially impermeable to said H+ ions.

15. The optical probe of claim 8 wherein said optical element comprises a plastic fiber optic.

* * * * *

UNITED STATES PATENT AND TRADEMARK OFFICE
CERTIFICATE OF CORRECTION

PATENT NO. : 5,251,633

DATED : October 12, 1993

INVENTOR(S) : Wunderling et al.

It is certified that error appears in the above-identified patent and that said Letters Patent is hereby corrected as shown below:

In the Abstract, line 10, change "hydrogen ions" to --hydrogen ions.--

Column 2, line 37, change "$HCO_3$" to --$HCO_3^-$-- and change "2H" to --$2H^+$--.

Column 3, line 6, after "as well" delete "30".

Column 3, line 15, change "adhesive means" to --adhesive means.--

Column 4, line 8, change "$HCO_3$" to --$HCO_3^-$--.

Column 4, line 60, change "H communication" to --$H^+$ communication--.

Signed and Sealed this

Ninth Day of August, 1994

Attest:

BRUCE LEHMAN

Attesting Officer    Commissioner of Patents and Trademarks